(12) United States Patent
Hashimoto et al.

(10) Patent No.: US 6,365,381 B2
(45) Date of Patent: Apr. 2, 2002

(54) METHOD FOR PRODUCING OPTICALLY ACTIVE COMPOUND

(75) Inventors: Shin-ichi Hashimoto, Machida; Ryoichi Katsumata, Sendai, both of (JP)

(73) Assignee: Kyowa Hakko Kogyo, Ltd., Tokyo (JP)

( * ) Notice: Subject to any disclaimer, the term of this patent is extended or adjusted under 35 U.S.C. 154(b) by 0 days.

(21) Appl. No.: 09/764,315

(22) Filed: Jan. 19, 2001

Related U.S. Application Data (62) Division of application No. 09/092,063, filed on Jun. 5, 1998, now Pat. No. 6,207,427.

(30) Foreign Application Priority Data

Jun. 9, 1997 (JP) ............................................. 9-150913

(51) Int. Cl.[7] .......................... C12P 13/24; C12N 15/70
(52) U.S. Cl. ................ 435/107; 435/252.33; 435/320.1
(58) Field of Search ............................. 435/107, 320.1, 435/252.33

(56) References Cited

U.S. PATENT DOCUMENTS

| 4,500,640 A | 2/1985 | Katsumata et al. ......... 435/253 |
| 5,374,542 A | 12/1994 | Katsumata et al. ......... 435/107 |
| 5,484,716 A | 1/1996 | Katsumata et al. ......... 435/108 |
| 5,559,016 A | 9/1996 | Katsumata et al. ......... 435/116 |
| 5,607,848 A | 3/1997 | Katsumata et al. ......... 435/143 |
| 5,643,769 A | 7/1997 | Katsumata et al. ......... 435/106 |

FOREIGN PATENT DOCUMENTS

| EP | 0 370 205 | 3/1996 |
| JP | 63-218621 | 9/1988 |
| JP | 5-111388 | 5/1993 |

OTHER PUBLICATIONS

Cancer Research, 48, 2483–2491, 1988.
J.Mol. Biol. 16, 118–133 (1966).
Biochimicha Biophys. Acta. 72, 619–629 (1963).
Methods in Enzymology, 272–285 (1971).
Methods in Enzymology, 632–637 (1971).
Tetrahedron Letters 28, 1277–1280 (1987).
Stryer, Biochemistry, 3$^{rd}$ Edition, pp. 388–389, 1988.
Maloy et al, J. Bacteriol, 1982, vol. 149, pp. 173–180.
Meloche et al., Biochem Biophys Res Comm, 1975, vol. 65, pp. 1033–1039.

*Primary Examiner*—Charles L. Patterson, Jr.
(74) *Attorney, Agent, or Firm*—Antonelli, Terry, Stout & Kraus, LLP (57) ABSTRACT

The present invention provides a method for industrially advantageously producing (S)-4-hydroxy-2-ketoglutaric acid and for producing compounds which are formed by biosynthesis from the precursor (S)-4-hydroxy-2-ketoglutaric acid, for example, for producing the compounds (2S,4S)-4-hydroxy-L-glutamic acid and (2S,4S)-4-hydroxy-L-proline, using a recombinant microorganism carrying a recombinant DNA harboring the DNA fragment encoding 4(S)-4-hydroxy-2-ketoglutaric acid aldolase gene.

12 Claims, 3 Drawing Sheets

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
caaaagctta tgaaaaactg gaaaac                                        26

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
tttggatcct tacagcttag cgcc                                          24

<210> SEQ ID NO 3
<211> LENGTH: 22
<212> TYPE: DNA
<213> ORGANISM: Artificial Sequence
<220> FEATURE:

```
<223> OTHER INFORMATION: Description of Artificial Sequence:synthetic
      DNA

<400> SEQUENCE: 3
gacccgtgct aatatggaag ac                                              22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
gtcttccata ttagcacggg tc                                              22
```

METHOD FOR PRODUCING OPTICALLY ACTIVE COMPOUND

CROSS-REFERENCE TO RELATED APPLICATIONS

This application is a divisional of Ser. No. 09/092,063, filed Jun. 5, 1998 now U.S. Pat. No. 6,207,427.

BACKGROUND OF THE INVENTION

FIELD OF THE INVENTION

The present invention relates to a method for producing (S)-4-hydroxy-2-ketoglutaric acid and to methods for producing compounds which can be formed from a precursor (S)-4-hydroxy-2-ketoglutaric acid, e.g., compounds such as (2S,4S)-4-hydroxy-L-glutamic acid and (2S,4S)-4-hydroxy-L-proline. (2S,4S)-4-hydroxy-L-proline has biological activities including anti-tumor cell activity [Cancer Res.48., 2483(1988)] and anti-mast cell activity (Japanese Unexamined Patent Publication No. 63-218621). (S)-4-hydroxy-2-ketoglutaric acid and (2S,4S)-4-hydroxy-L-glutamic acid are useful for the production of (2S,4S)-4-hydroxy-L-proline.

As a conventional method for producing (S)-4-hydroxy-2-ketoglutaric acid, a number of methods have been known, including a chemical deamination of threo-4-hydroxy-L-glutamic acid [Methods in Enzymology, 17 part B, 275].

The present inventors previously disclosed a method for producing (S)-4-hydroxy-2-ketoglutaric acid (Japanese Unexamined Patent Publication No. 7-289284), comprising allowing (e.g., providing) a biocatalyst, having activity to generate (S)-4-hydroxy-2-ketoglutaric acid from pyruvic acid, to act on glyoxylic acid and pyruvic acid or a compound capable of being converted into pyruvic acid through the action of the biocatalyst. Compared with the methods conventionally known, the method is far more industrially advantageous., but the method is disadvantageous in that the accumulation of (S)-4-hydroxy-2-ketoglutaric acid is less if inexpensive glucose is used as the substrate, and that expensive pyruvic acid should necessarily be used as the substrate so as to yield an accumulation level of (S)-4-hydroxy-2-ketoglutaric acid above 20 mM.

The following conventional methods for producing (2S,4S)-4-hydroxy-L-glutamic acid have been known; a method comprising allowing glutamate dehydrogenase to act on chemically synthesized DL-4-hydroxy-2-ketoglutaric acid in the presence of ammonia and NADPH and separating the resulting 4(R)- and 4(S)-4-hydroxy-glutamic acid by ion exchange chromatography; a method comprising extracting (2S,4S)-4-hydroxy-L-glutamic acid from a plant (Phlox decussata) [Methods in Enzymology, 17 part B, 277]; and a method comprising allowing transaminase to act on L-4-hydroxy-2-ketoglutaric acid and cysteine sulfinic acid [Tetrahedron Letters, 28, 1277 (1987)].

The present inventors have previously disclosed a method for producing (2S,4S)-4-hydroxy-L-glutamic acid, comprising allowing (e.g., providing) a biocatalyst, having activity to generate (2S,4S)-4-hydroxy-L-glutamic acid from pyruvic acid and glyoxylic acid in the presence of an amino group donor, to act on glyoxylic acid and pyruvic acid or a compound capable of being converted into pyruvic acid (Japanese Unexamined Patent Publication No. 8-80198). The method is industrially advantageous in that only the 4(S) form can be produced; however, the method is laborious and disadvantageous in that the method further requires a step of converting (S)-4-hydroxy-L-ketoglutamic acid into (2S,4S)-4-hydroxy-L-glutamic acid by adding another bacterium to (S)-4-hydroxy-L-ketoglutamic acid after the step of synthesis of (S)-4-hydroxy-L-ketoglutamic acid so as to produce a great amount of (2S,4S)-4-hydroxy-L-glutamic acid by the method.

As a conventional method for producing (2S,4S)-4-hydroxy-L-proline, the following methods have been known; a method comprising culturing a microorganism of genus Helicoceras or Acrocylindrium and extracting proline from the culture (Japanese Unexamined Patent Publication No. 5-111388); and a method comprising allowing (e.g., providing) a microorganism, having activity to convert 4-hydroxy-2-ketoglutaric acid into 4-hydroxy-L-proline, to act on 4-hydroxy-2-ketoglutaric acid (Japanese Unexamined Patent Publication No. 3-266996); and the like. However, the industrial application of these methods is difficult, because the yield of the former method is low and the latter method requires laborious procedures for separation and purification of the simultaneously generated 4(S) form and 4(R) form.

SUMMARY OF THE INVENTION

An object of the present invention is to provide a method for industrially advantageously producing (S)-4-hydroxy-2-ketoglutaric acid and compounds produced from the precursor (S)-4-hydroxy-2-ketoglutamic acid, for example (2S,4S)-4-hydroxy-L-glutamic acid and (2S,4S)-4-hydroxy-L-proline.

The present invention relates to a method for producing an optically active compound, comprising allowing (e.g., providing) a recombinant microorganism, carrying recombinant DNA including a DNA fragment encoding (S)-4-hydroxy-2-ketoglutarate aldolase (abbreviated as "KAL gene" hereinbelow), to act on sugar and glyoxylic acid in the presence or absence of an amino group donor in an aqueous medium and collecting optically active (S)-4-hydroxy-2-ketoglutaric acid generated in the aqueous medium or a compound produced from the precursor (S)-4-hydroxy-2-ketoglutaric acid (abbreviated as "4(S)KHG" hereinbelow).

DETAILED DESCRIPTION OF THE INVENTION

The present invention relates to a method for producing (S)-4-hydroxy-2-ketoglutaric acid (4(S)KHG) or to a method for producing a compound which can be formed from the precursor 4(S)KHG.

The compound, which can be produced from the precursor (S)-4-hydroxy-2-ketoglutaric acid, includes (2S,4S)-4-hydroxy-L-glutamic acid [abbreviated as "4(S)HG" hereinbelow], (2S,4S)-4-hydroxy-L-proline [abbreviated as "4(S)HYP" hereinbelow], (S)-4-hydroxy-L-glutamine, (S)-4-hydroxy-L-arigine, (S)-4-hydroxy-L-ornithine, and the like. (S)-4-hydroxy-L-glutamine, (S)-4-hydroxy-L-arigine, (S)-4-hydroxy-L-ornithine are useful as a feed additive for animals.

According to the present invention, the compound can be formed directly, using the microorganism carrying the recombinant DNA harboring the KAL gene (i.e., the precursor 4(S)KHG need not be formed as an intermediate). Or, the microorganism can be used as a biocatalyst to convert the precursor 4(S)KHG to the compound. By referring to the compound from a precursor 4(S)KHG herein, we mean either technique for forming the compound.

The method for producing 4(S)KHG, 4(S)HG and 4(S)HYP using a microorganism carrying a recombinant DNA harboring the KAL gene is described below.

The KAL gene includes such gene derived from microorganisms of genus Escherichia, Pseudomonas, Paracoccus, Providencia, Rhizobium or Morganella; the KAL gene is preferably the gene from genus Escherichia. The method for recovering the KAL gene from, for example, genus Escherichia is now specifically described.

From a microorganism having activity of 4-hydroxy-2-ketoglutarate aldolase, for example *E. coli* strain W3110 (ATCC 14948), the chromosomal DNA is prepared by a conventional method [Biochim. Biophys. Acta., 72, 619 (1963)]. Based on the nucleotide sequence published in a reference [R. V. Patil and E. E. Dekker, J. Bacteriol. 174, 102 (1992)], an oligonucleotide primer is synthesized. Subsequently, polymerase chain reaction (abbreviated as "PCR" hereinbelow) [R. F. Saiki et al., Science 230, 1350 (1985)] is conducted on a template of the resulting chromosomal DNA to obtain the above gene.

To introduce the KAL gene into a host, for example, *Escherichia coli*, any vector may be used, including phage vector, plasmid vector and the like, as long as the vector can be autonomously replicated or can incorporate the gene into the chromosome of a host microorganism. Vectors suitable for a *Escherichia coil* host include pBR322, pUC119, pACY184 and pTrS33 (Japanese Unexamined Patent Publication No. 2-227075) carrying trp promoter. A vector suitable for a host of a microorganism of genus Corynebacterium includes a vector from pCG1.

A recombinant DNA from the KAL gene and a vector DNA can be prepared together with various recombinant mixtures, by digesting the two DNAs in vitro with restriction enzymes having the same restriction site, and subjecting the digested products to ligation with DNA ligase. Using the resulting recombinant mixture, the host microorganism is transformed and a transformant strain having activity to catalyze the reaction to generate 4(S)KHG from pyruvic acid and glyoxylic acid is selected, whereby the recombinant DNA can be obtained from the strain. Such recombinant DNA specifically includes pKSR101, pKSR125 and pKSR601. Transformation can be carried out according to known methods, for example, molecular cloning as described in Molecular Cloning, T. Maniatis et al., Cold Spring Harbor Laboratory, 1982.

A recombinant microorganism carrying a recombinant DNA harboring the KAL gene can be prepared, by incorporating a DNA fragment carrying the genetic information into the vector DNA to prepare a recombinant DNA, and subsequently transforming a host microorganism with the resulting recombinant DNA. As such host microorganism, any microorganism may be usable, as long as the microorganism can incorporate the recombinant DNA and can express enzyme activity to catalyze the reaction to generate 4(S)KHG from pyruvic acid and glyoxylic acid on the basis of the genetic information. The microorganism may include, for example, microorganisms of genus Escherichia or Corynebacterium. More specifically, the microorganism includes for example strain ATCC 33625 of *Escherichia coli* K-12, *Corynebacterium glutamicum* ATCC13032, and *Corynebacterium acetoacidophilum* FERM P-4962.

To produce 4(S)KHG, 4(S)HG or 4(S)HYP using the recombinant microorganism carrying the recombinant DNA harboring the KAL gene, a microorganism having at least one property of possessing a lipoate requirement or possessing a reduction or loss of malic acid synthase activity is preferably used as the host microorganism.

As such microorganism, any microorganism capable of incorporating the recombinant DNA and expressing the enzyme activity to catalyze the reaction to generate 4(S)KHG from pyruvic acid and glyoxylic acid on the basis of the genetic information may be used, including for example microorganisms of genus Escherichia or Corynebacterium. More specifically, the microorganism includes for example strain ATCC 33625 of *Escherichia coli* K-12, *Corynebacterium glutamicum* ATCC 13032, and *Corynebacterium acetoacidophilum* FERM P-4962.

More specifically, an *Escherichia coli* K-12 sub-strain NHK40 [lipoate requirement (lip), 4KAL deletion (eda)] may be used. The strain NHK40 was deposited with the National Institute of Bioscience and Human-Technology, Agency of Industrial Science and Technology in Japan on Apr. 16, 1997 as FERM BP-5919 under the Budapest Treaty.

To produce 4(S)HG, a microorganism in which phosphoenolpyruvate carboxylase activity is deleted is preferably used as the host microorganism.

As such microorganism, any microorganism capable of incorporating the recombinant DNA-and expressing the enzyme activity to catalyze the reaction to generate 4(S)KHG from pyruvic acid and glyoxylic acid on the basis of the genetic information may be used, including for example microorganisms of genus Escherichia or Corynebacterium. More specifically, the microorganism includes, for example, strain ATCC 33625 of *Escherichia coli* K-12, *Corynebacterium glutamicum* strain ATCC 13032, and *Corynebacterium acetoacidophilum* FERM P-4962.

More specifically, an *Escherichia coli* K-12 sub-strain NHK46 [lip, eda, malic acid synthase deletion (glc), phosphoenolpyruvate carboxylate deletion (ppc)] may be used. The *Escherichia coli* NHK46 was deposited with the National Institute of Bioscience and Human-Technology, Agency of Industrial Science and Technology in Japan on Apr. 16, 1997 as FERM BP-5920 under the Budapest Treaty.

To produce 4(S)HYP, alternatively, a microorganism having at least one property of a lipoate requirement, the reduction or deletion of malic acid synthase activity and deletion of phosphoenolpyruvate carboxylase activity and being resistant to proline analogs is more preferably used. Such proline analogs include azetidine-2-carboxylic acid, 3,4-dehydroproline and thioproline.

As such microorganism, any microorganism capable of incorporating the recombinant DNA and expressing the enzyme activity to catalyze the reaction to generate 4(S)KHG from pyruvic acid and glyoxylic acid on the basis of the genetic information may be used, including for example microorganisms of genus Escherichia or Corynebacterium. More specifically, the microorganism includes strain ATCC 33625 of *Escherichia coli* K-12, *Corynebacterium glutamicum* strain ATCC 13032, and *Corynebacterium acetoacidophilum* FERM P-4962.

More specifically, an *Escherichia coli* K-12 sub-strain NHK47 [having lip, eda., glc, ppc, and anti-azetidine-2-carboxylate resistance] is mentioned. The *Escherichia coli* strain NHK47 was deposited with the National Institute of Bioscience and Human-Technology, Agency of Industrial Science and Technology in Japan on Apr. 16, 1997 as FERM BP-5921 under the Budapest Treaty.

The various deletion strains or resistant strains mentioned above may be strains of wild type having the properties described above, or may be obtained by subjecting their parent strains with no such properties to conventional mutation process such as treatment with mutation agents for example N-methyl-N'-nitro-N-nitrosoguanidine (NTG), UV irradiation or γ irradiation, coating the resulting strains on an appropriate agar plate medium, harvesting a grown mutant strain, and selecting a strain with the deletion or reduction of the objective enzyme activity compared with the parent strains or harvesting a strain more resistant to the analogs than the parent strains. Transducing the deletion mutation (transduction) from a strain with the objective deletion or resistance mutation into a desirable strain, using phage P1, allows recovery of various deletion mutant strains and resistance mutant strains for strains of the *Escherichia coli* K-12 [J. H. Miller, Experiments in Molecular Genetics, Cold Spring Harbor, Laboratory (1972)].

The microorganism to be used in accordance with the present invention can be cultured by conventional culturing procedures. The culture medium to be used for such culturing may be any natural medium or any synthetic medium, as long as the medium contains carbon source, nitrogen source, inorganic salts and the like, which can be assimilated by the microorganism to be used, whereby the microorganism can be cultured efficiently. Any carbon source which can be assimilated by the microorganism to be used may be usable, including sugars such as glucose, fructose, sucrose, maltose, starch, starch hydrolysate, and molasses; organic acids such as acetic acid, lactic acid and gluconic acid; or alcohols such as ethanol and propanol. Any nitrogen source which can be assimilated by the microorganism may be usable, including inorganic salts such as ammonia, ammonium sulfate, ammonium chloride, and ammonium phosphate; ammonium salts of organic acids, peptone, casein hydrolysate, meat extract, yeast extract, corn steep liquor, soy bean bran, soy bean bran hydrolysate, various fermentation bacteria and digestion products of the bacteria. Any inorganic salt which can be assimilated by the microorganism may be usable, including potassium phosphate, ammonium sulfate, ammonium chloride, sodium chloride, magnesium sulfate, ferrous sulfate and manganese sulfate. Additionally, salts of calcium, zinc, boron, copper, cobalt and molybdenum may be added as trace elements. If necessary, the culture medium may contain vitamins such as for example thiamin and biotin, amino acids such as glutamic acid and aspartic acid, and nucleic acidrelated substances such as adenine and guanine. Culturing is carried out under aerobic conditions, by agitation culture or submerged aeration agitation culture. The culturing is carried out at preferably 20 to 45° C. for 10 to 96 hours at pH 5.0 to 9.0. The pH is adjusted with inorganic or organic acids, alkaline solutions, urea, calcium carbonate, and ammonia. The culture thus produced may be used as it is for the objective reaction; in the alternative, the culture may be treated, and the resulting treated product may be subjected to the subsequent reaction. The treated product includes the forms of condensate and dried product, freeze-dried product, surfactant-treated product, organic solvent-treated product, thermally treated product, enzymatically treated product, ultrasonication-treated product and mechanical disruption-treated product of the culture, and immobilized products of the bacteria or treated products of the bacteria.

Examples of the aqueous medium to be used in the present invention include water; buffers such as phosphate, carbonate, acetate, borate, citrate, and Tris; and aqueous solutions containing organic solvents including alcohols such as methanol and ethanol; esters such as ethyl acetate; ketones such as acetone; and amides such as acetamide. If necessary, furthermore, surfactants such as Triton X-100 (Nacalai Tesque, Inc.) and Nonion HS204 (NOF Corporation), as well as organic solvents such as toluene and xylene, may be added at about 0.1 to 20 g/liter into the medium.

The amino group donor to be used in accordance with the present invention includes ammonia; inorganic ammonium salts such as ammonium sulfate, ammonium chloride, and urea; and various amino acids such as glutamic acid. The concentration of the amino group donor is 0.1 to 100 g/liter, preferably 1 to 50 g/liter.

The concentration for production of 4(S)KHG by allowing the recombinant microorganism carrying the recombinant DNA harboring the KAL gene to act on sugar and glyoxylic acid, is generally 5 to 100 g/liter. The concentrations of sugar and glyoxylic acid are both 1 to 200 g/liter, preferably 20 to 200 g/liter. Any sugar which can be assimilated by the recombinant strain may be usable, including glucose, fructose, sucrose, maltose, starch, starch hydrolysate and molasses The reaction is carried out at 15 to 80° C., preferably 25 to 60° C., at a pH of 3 to 11, preferably a pH of 5 to 9, for 1 to 96 hours.

In the above process, 4(S)KHG may be prepared by adding glyoxylic acid at the concentration mentioned above, at the starting point or in the course of the culturing of a microorganism carrying the recombinant DNA harboring the KAL gene. Sugar may be added in advance as the culture substrate or may be added together with glyoxylic acid.

The resulting 4(S)KHG may be isolated and purified by conventional purification processes of organic acids. From the reaction supernatant from which solids are removed by centrifuge, for example, 4(S)KHG can be isolated and purified by a process by means of ion exchange resin and membrane process in combination.

As the sugar used for producing 4(S)HG or 4(S)HYP by allowing the recombinant microorganism carrying the recombinant DNA harboring the KAL gene to act on sugar and glyoxylic acid in an aqueous medium in the presence of an amino group donor, any sugar which can be assimilated by the recombinant strain may be used, including glucose, fructose, sucrose, maltose, starch, starch hydrolysate, and molasses. The bacterial concentration for the reaction is generally 5 to 100 g/l. The concentrations of sugar and glyoxylic acid are both 1 to 200 g/l, preferably 10 to 200 g/l. The reaction is carried out at 15 to 80° C., preferably 25 to 60° C. at a pH of 3 to 11, preferably a pH of 5 to 9, for 1 to 96 hours. In the process, 4(S)HG or 4(S)HYP may be prepared by adding glyoxylic acid at the concentration mentioned above at the starting point of or in the course of the culturing of a microorganism carrying the recombinant DNA harboring the KAL gene.

Additionally, 4(S)HYP may also be produced by adding a biocatalyst having activity to convert 4(S)KHG into 4(S) HYP, with 4(S)KHG in the presence of an amino group donor to an aqueous medium.

An example of the use of 4(S)KHG for producing 4(S) HYP include isolated and purified 4(S)KHG, a crude sample thereof which contains no 4(R)KHG or 4(R)HG therein, and a reaction solution containing 4(S)KHG formed through the reaction of a biocatalyst. The concentration of 4(S)KHG is 1 to 200 g/liter, preferably 20 to 200 g/liter.

Examples of the biocatalyst having activity of converting 4(S)KHG into 4(S)HYP in the presence of the amino group donor include cells, a culture and processed cells of microorganisms having activity of converting 4(S)KHG into 4(S)HYP. Such microorganisms include microorganisms of genus Escherichia and Corynebacterium. More specifically, the microorganisms include strain ATCC 33625 of *Escherichia coli* K-12, which is prepared by modifying proBA gene (encoding proB and proA) coding for the enzyme of proline synthesis in *Escherichia coli* and then preparing plasmid pKSR25 carrying the resulting mutant proBA gene with reduced feed back inhibition, and thereafter introducing the plasmid into an *Escherichia coli* strain. More preferably, a mutant strain with a glutamic acid requirement is mentioned. Such a mutant strain can be prepared by subjecting its parent strain to conventional mutagenesis technique, for example, N-methyl-N'-nitro-N-nitrosoguanidine (NTG), UV irradiation or γ irradiation, coating the resulting strains on an appropriate agar plate medium, harvesting a grown mutant strain, and selecting a strain with glutamic acid requirement for the growth. In a case of a microorganism of *Escherichia coli* K-12, furthermore, a deletion mutant strain can also be produced by transduction. Such a microorganism includes NHK3/pKSR25 strain, which is prepared by first obtaining an isocitrate dehydrogenase deletion mutation (icd) of strain ATCC 33625 of *Escherichia coli* K-12 to obtain strain NHK3, and subsequently introducing pKSR25 into strain NHK3; such a microorganism also includes strain (NHK3/pKSR25+pKSR50), with plasmid pKSR50 additionally containing glutamate dehydrogenase and glucose-6-phosphate dehydrogenase having been introduced therein. A host microorganism with a glutamic acid requirement and with resistance to azetidine-2-carboxylic acid and proline analogs such as 3,4-dehydroproline and thioproline is more advantageously used. Such microorganism can be obtained by subjecting its parent strain to mutagenesis and transduction; additionally, the microorganism can be obtained by introducing a plasmid having proline analog resistance into the parent strain. More specifically, *Escherichia coli* strain NHK23/pKSR25+pKSR50 is mentioned. *Escherichia coli* strains NHK3/pKSR25+pKSR50 and *Escherichia coli* strain NHK23/pKSR25+pKSR50 were deposited with the National Institute of Bioscience and Human-Technology, Agency of Industrial Science and Technology in Japan on Apr. 16, 1997 as FERM BP-5922 and BP-5923, respectively, under the Budapest Treaty.

The concentration of the biocatalyst to be used for the reaction is generally 5 to 100 g/liter. The reaction is carried out at 15 to 80° C., preferably 25 to 60° C. at a pH of 3 to 11, preferably a pH of 5 to 9, for 1 to 96 hours. 4(S)HYP is produced by adding 4(S)KHG at the starting point of or in the course of culturing of a microorganism having activity of converting 4(S)KHG into 4(S)HYP in the presence of the amino group donor.

4(S)HG or 4(S)HYP thus produced can be isolated by conventional purification methods for amino acids. By a combination of an ion exchange resin and a membrane process, for example, 4(S)HG or 4(S)HYP can be isolated from a reaction supernatant from which solids are preliminarily removed-by centrifugation.

EXAMPLES

The present invention will now be described in more detail in the following examples. Unless otherwise specified, the general procedures for recombinant DNA were according to the method described in Molecular Cloning, A Laboratory Manual, T. Maniatis et al., Cold Spring Harbor Laboratory, 1982.

Example 1

Preparation of Plasmid Containing KAL Gene

One platinum loop of strain W 3110 (ATCC 14948) of *Escherichia coli* K-12 was inoculated in a 10-ml LB liquid medium [containing Bactotrypton (10 g; manufactured by Difco, Co.), yeast extract (5 g; manufactured by Difco, Co.) and NaCl (5 g) per one liter of water and having been adjusted to pH 7.2], for culturing at 30° C. for 20 hours. From the cultured microorganisms was isolated chromosomal DNA by a known method [H. Saito & K. I. Miura, Biochim. Biophys. Acta., 72, 619(1963)].

Based on the nucleotide sequence of the KAL gene as reported [R. V. Patil and E. E. Dekker, J. Bacteriol. 174, 102(1992)], an oligonucleotide of the DNA sequence of SEQ. ID No:1 corresponding to the N terminus of the genetic product and an oligonucleotide of the DNA sequence of SEQ. ID No:2 corresponding to the C terminus of the KAL gene were individually synthesized by conventional methods. Using these oligonucleotides as the primers, the KAL gene was amplified by PCR [R. F. Saiki, et al., Science 230, 1350 (1985)]. Using the isolated chromosomal DNA of the *Escherichia coli* W 3110 (ATCC 14948) as the template, amplification was conducted with Gene Amp™ kit (manufactured by Perkin Elmer, Japan) and a DNA thermal cycler manufactured by the same Company, for 30 cycles of each cycle composed of 94° C. for 30 seconds, 52° C. for 30 seconds and 72° C. for one minute, followed by reaction at 72° C. for 5 minutes. After the termination of the reaction, the amplified DNA fragment of about 630 bps was extracted with chloroform and purified through ethanol precipitation. The DNA fragment (2 μg) and vector plasmid pTrS33 (1 μg) (Japanese Unexamined Patent Publication No. 2-227075) carrying the trp promoter were independently digested with HindIII and BamHI in a double fashion, and were then purified by agarose gel electrophoresis. The purified two fragments were mixed together, prior to ethanol precipitation, and the resulting mixture was then dissolved in distilled water (5 μl) and subjected to ligation, to prepare recombinant DNA.

The recombinant DNA obtained was used to transform the *Escherichia coli* ATCC 33625 using the method of Maniatis et al. [Molecular Cloning, A Laboratory Manual, Cold Spring Harbor Laboratory (1982)], and the resulting strains were then smeared on an LB agar culture medium containing 100 μg/ml ampicillin, and incubated at 37° C. for 24 hours. The resulting eight ampicillin-resistant transformant colonies were assayed for activity to synthesize 4-hydroxy-2-ketoglutaric acid from pyruvic acid and glyoxylic acid. More specifically, each transformant strain was cultured in an LB liquid medium (3 ml) containing 100 μg/ml ampicillin at 30° C. for 20 hours, followed by addition of xylene (30 μl), 2M sodium pyruvate (150 μl) and 2M glyoxylic acid solution (150 μl; adjusted to pH 6.4 by using NaOH) to the culture solution, with shaking at 37° C. for 30 minutes. The supernatant from the centrifuged reaction solution was assayed by high-performance liquid chromatography (HPLC), to measure the yield of 4(R)- and 4(S)-4-hydroxy-2-ketoglutaric acids.

HPLC Assay Conditions

Column; SUMICHIRAL OA-5000 column, manufactured by Sumitomo Chemical Assay Center, Co.

Mobile phase; a mixture solution of a pair of 1 mM copper (II) sulfate and aqueous 0.1 mM ammonium acetate solution (pH 4.5) and isopropanol at 85:15, in this order.

Flow rate; 1 ml/min

Temperature; 40° C.

Detection; absorbance at UV 210 nm.

Figure 1:
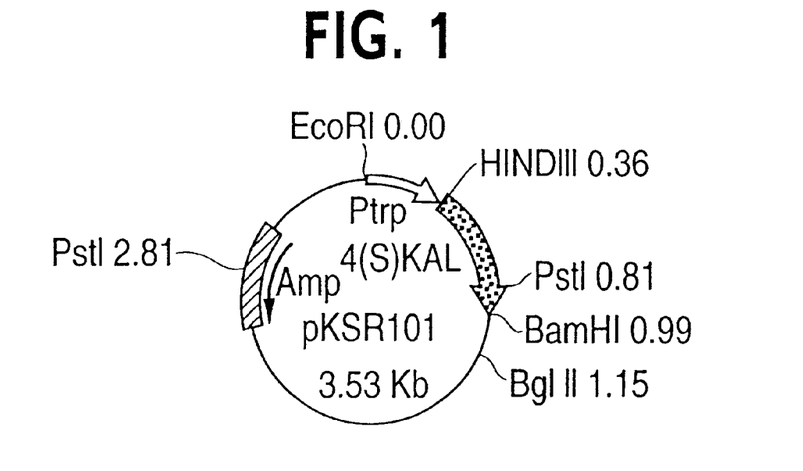
FIG. 1 depicts plasmid pKSR101 and a restriction map of the plasmid.

As a result, the ability to actively synthesize 4(S)KHG was observed in any of the transformants. Additionally, these strains were cultured with agitation in an LB liquid medium (3 ml) containing 100 μg/ml ampicillin at 37° C. for 16 hours prior to centrifugation, and plasmids were isolated from the resulting microorganisms according to the known method [Molecular Cloning, A Laboratory Manual, Cold Spring Harbor Laboratory (1982)], and digested with various restriction enzymes to determine the structures. It was observed that all these plasmids had the same structure. The plasmid thus prepared was defined as pKSR101. The restriction map of pKSR101 is shown in FIG. 1. With respect to pKSR101, the *Escherichia coil* NHK46/pKSR101, which carries pKSR101, was deposited with the National Institute of Bioscience and Human-Technology, Agency of Industrial Science and Technology in Japan on Jun. 2, 1998 as FERM BP-6382 under the Budapest Treaty.

Figure 2:
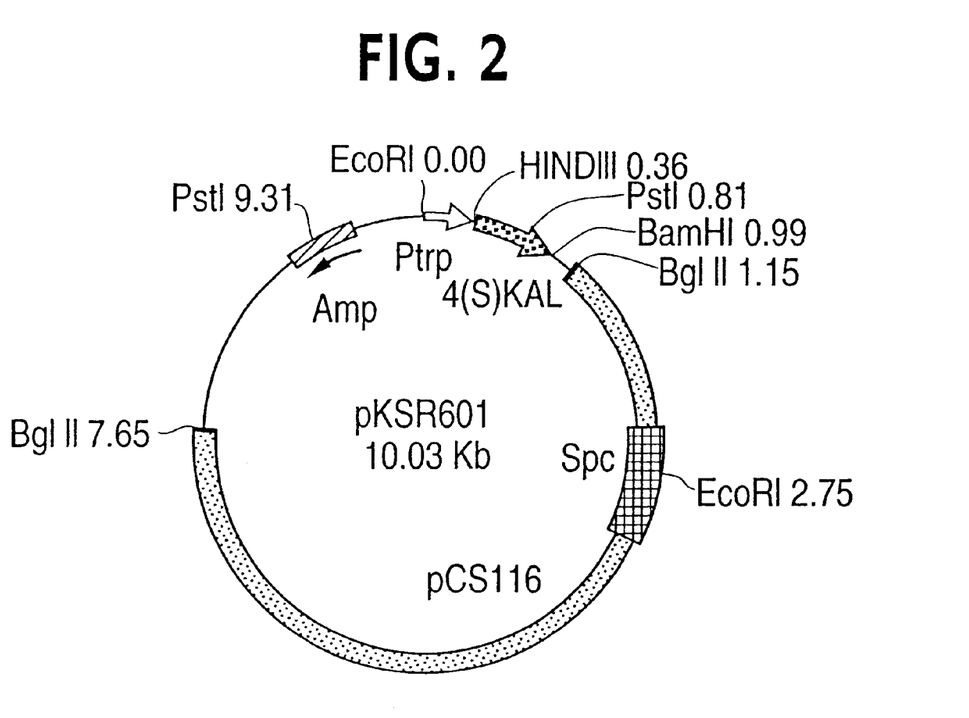
FIG. 2 depicts plasmid pKSR601 and a restriction map of the plasmid.

To introduce 4(S)KAL gene into a microorganism of genus Corynebacterium, the pKSR 101 was ligated to a vector plasmid pCS116 (Japanese Unexamined Patent Publication No. 6-277082) autonomously replicable. pCS 116 (1 μg) and pKSR101 (1 μg) were dissolved in H buffer (45 μl; manufactured by Takara Brewery), to which was added 10 units of Bgl II for digestion at 37° C. for 3 hours, followed by phenol extraction and ethanol precipitation. The resulting matter was dissolved in distilled water (5 μl) for ligation, to prepare a recombinant DNA. Using the recombinant DNA, the *Escherichia coil* ATCC 33625 was transformed by the method of Maniatis et al. [Molecular Cloning, A Laboratory Manual, Cold Spring Harbor Laboratory (1982)]. The resulting strains were smeared on an LB agar culture medium containing 100 μg/ml ampicillin and 100 μg/ml spectinomycin and incubated at 37° C. for 24 hours. From the resulting colonies resistant to ampicillin and spectinomycin, plasmids were isolated in the same manner as described above, and *Corynebacterium glutamicum* ATCC 13032 was transformed with the plasmid by the known method (Japanese Unexamined Patent Publication No. 6-277082). The transformant was then smeared on a BY agar culture medium containing 100 μg/ml glutamicum [the medium contained bouillon (20 g; manufactured by Kyokuto Co.) and yeast extract (5 g; manufactured by Kyokuto Co.) in water of one liter and having been preliminarily adjusted to pH 7.2 and solidified through the addition of 2% agar], and incubated at 30° C. for 48 hours. By the known method (Japanese Unexamined Patent Publication No. 57-183799), plasmids were isolated from the eight resulting spectinomycin-resistant colonies to determine the structure. As a result, it was observed that all these plasmids had the same structure. The plasmid thus prepared was defined as pKSR601. The restriction map of pKSR601 is shown in FIG. 2.

Example 2

Preparation of 4(S)KHG in Mutant Strain of *Escherichia coli*

A ppc Mutation was given to a strain WA802 of *Escherichia coli* K-12 [J. Mol. Biol. 16, 118 (1966)], through transduction using P1 phage from a strain DV21A05 with ppc mutation of *Escherichia coli* K-12 strain [J. Bacteriol. 132, 832(1977)], and by further using the transduction process by means of the P1 phage, a lip mutation was given and an eda mutation was subsequently given to the strain, to prepare a strain NHK42 with mutation of ppc, lip and eda triple deletions. From the strain NHK 42, a strain with reduced malic acid synthase activity was induced. The microorganisms of the strain NHK42 cultured up to the logarithmic growth stage in an LB medium containing 2 g/l glutamic acid and 100 μg/l lipoic acid, were centrifuged and harvested, rinsed in 0.05M Tris-maleate buffer solution (pH 6.0), and suspended in the buffer solution to a final bacterial concentration of $10^9$ cells/ml. NTG was added into the suspension to a final concentration of 600 mg/l, and the resulting mixture was retained at ambient temperature for 20 minutes for mutagenesis. After the mutagenesis, the microorganisms were smeared on an M9 minimal agar culture medium with addition of 0.5% glucose, 0.05 g/l glutamic acid, 100 μg/l lipoic acid, and 30 mM glyoxylic acid [Molecular Cloning, A Laboratory Manual, Cold Spring Harbor Laboratory (1982)]. After 2-day incubation at 37° C., small colonies among the generated colonies were collected in an LB agar culture medium with addition of 2 g/l glutamic acid and 100 μg/l lipoic acid. The collected mutant strains were replicated in an M9 minimal agar culture medium with addition of 0.5% glucose, 0.5 g/l glutamic acid and 100 μg/l lipoic acid, and in an M9 minimal agar culture medium with addition of 0.5% glucose, 100 μg/l lipoic acid, and 30 mM glyoxylic acid. Then, strains growing in the former medium but never growing in the latter medium were selected. The selected strains were cultured with agitation in an MS medium [the medium contained 3 g glucose, 4 g $KH_2PO_4$, 10 g $(NH_4)_2SO_4$, 1 g $MgSO_4$, 100 μg thiamin hydrochloride, 1 g yeast extract, 1 g peptone, 50 μg lipoic acid, 20 g $CaCO_3$, and 2 g glutamic acid per one liter of water and had been adjusted to pH 7.2] at 37° C. At the later stage of the logarithmic growth, the microorganisms were harvested and rinsed in 50 mM Tris-hydrochloric acid buffer (pH 7.0), and the microorganisms were then disrupted with an ultrasonication disrupting machine and centrifuged at 15,000 rpm for 45 minutes, to obtain the supernatant, which was defined as cell extract solution. Using the cell extract solution, the malic acid synthase activity was assayed by a known reference [Methods in Enzymology 5, 633 (1962)]. A strain NHK 46 which was detected to have no activity was selected as the objective mutant strain.

Using the transduction process employing a P1 phage, the $lip^+$ gene was introduced from the *Escherichia coli* W 3110 (ATCC 14948) into the strain NHK 46, to prepare strain NHK 48 with no requirement of lipoic acid.

Using the method of Maniatis et al. [Molecular Cloning, A Laboratory Manual, Cold Spring Harbor Laboratory (1982)], pKSR101 was introduced into strains NHK 42, NHK 46 and NHK 48 (provided that culturing was conducted after 100 μg/l lipoic acid and 2 g/l glutamic acid were added to the medium), to obtain transformants using as the marker for ampicillin resistance.

Each transformant was cultured with agitation in an LB medium containing 1% glucose, 2% calcium carbonate, 100 μg/l lipoic acid, and 2 g/l glutamic acid at 28° C. for 16 hours. Each culture broth was added into a sterilized T medium of 5 ml [the medium contained 50 g glucose, 4 g $KH_2PO_4$, 10 g $(NH_4)_2SO_4$, 1 g $MgSO_2$, 10 μg thiamin hydrochloride, 0.2 g yeast extract, 3 g KCl, 50 μg lipoic acid, 250 mg tryptophan, 20 g $CaCO_3$, and 2 g glutamic acid per one liter of water and had been adjusted to pH 7.2], at 30° C. for 24 hours, followed by addition of 0.25 ml of 2M glyoxylic acid solution (adjusted to pH 6.4 by using NaOH), prior to another 24-hour agitation culture at 37° C. The obtained culture broth was centrifuged, and the resulting culture supernatant was analyzed by HPLC to assay the yields of 4(R)KHG and 4(S)KHG. The results are shown in Table 1. As apparently shown in the yields of 4(S)KHG, the mutation for lipoate requirement and mutation for reduction of malic acid synthase activity make a contribution to the yield of 4(S)KHG.

TABLE 1

| Host | Plasmid | 4(R)KHG(mM) | 4(S)KHG(mM) |
|---|---|---|---|
| Escherichia coli NHK42 | pKSR101 | 0.8 | 7.5 |
| Escherichia coli NHK46 | pKSR101 | 3.1 | 28.1 |
| Escherichia coli NHK48 | pKSR101 | 0.0 | 0.0 |

Example 3

Production of 4(S)KHG in Corynebacterium Glutamicum

Corynebacterium glutamicum strain ATCC 13032 introduced with pKSR601 was cultured with agitation in an LB culture medium for 16 hours. The culture broth (0.5 ml) was added into a sterilized TC medium (5 ml) [the medium contained 10 g glucose, 0.5 g $KH_2PO_4$, 0.5 g $K_2HPO_4$, 20 g $(NH_4)_2SO_4$, 0.25 g $MgSO_4$, 3 g urea, 100 μg biotin, 5 g corn steep liquor, 10 mg $FeSO_4.7aq$, 5 mg $MNSO_4.4$–6aq, and 20 g $CaCO_3$ per one liter of water and had been adjusted to pH 7.2], and cultured with agitation at 30° C. for 24 hours. Then, 2M glyoxylic acid solution (0.25 ml; adjusted to pH 6.4 by using NaOH) was added thereto and the mixture was cultured with agitation at 37° C. for further 24 hours. The culture supernatant was analyzed by HPLC in the same manner as in Example 2. The yield of 4(S)KHG was 34.7 mM with no generation of 4(R)KHG.

Example 4

Scale up Production of 4(S)KHG

On the basis of the results in Example 2, pKSR101 was introduced into the strain NHK40 with double deletion mutation of lip and eda among the strains of Escherichia coli K-12 as in Example 2, to prepare a strain to generate 4(S)KHG. The transformant was cultured with agitation in an LB medium containing 1% glucose, 2% calcium carbonate and 100 μg/l lipoic acid at 28° C. for 13 hours. The culture broth (10 ml) was added to the same culture medium of 200 ml in a 1-liter sterilized Erlenmeyer flask and cultured with agitation at 28° C. for 13 hours. The total volume of the culture broth was added to the J1 culture medium of the composition shown in Table 2 in a 5-liter sterilized jar, and cultured at an aeration of 2 liter/min and agitation of 500 rpm and 33° C., while the pH of the medium was kept at pH 6.8 by using aqueous ammonia. Twenty hours later, xylene (20 ml) and 2M glyoxylic acid solution (adjusted to pH 6.4 by using NaOH) were added into the jar, and further cultured at 37° C. for 12 hours. The culture supernatant was analyzed by HPLC, and it was observed that the yield of 4(S)KHG was 305 mM.

TABLE 2

| Composition of J1 culture medium (per one liter; adjusted to pH 6.8) | |
|---|---|
| Glucose | 30 g |
| $KH_2PO_4$ | 2 g |
| $K_2HPO_4$ | 2 g |
| $(NH_4)_2SO_4$ | 10 g |
| $MgSO_4$ | 1 g |
| $FeSO_4.7aq$ | 10 mg |

TABLE 2-continued

| Composition of J1 culture medium (per one liter; adjusted to pH 6.8) | |
|---|---|
| $MnSO_4.4$–6aq | 10 mg |
| $CoCl_2$ | 1.5 mg |
| $CaCl_2$ | 15 mg |
| $NiCl_2$ | 1.5 mg |
| Ammonium molybdate | 1.5 mg |
| Thiamin hydrochloride salt | 100 μg |
| Yeast extract | 0.5 g |
| KCl | 3 g |
| Lipoic acid | 75 μg |
| Tryptophan | 250 mg |

Example 5

Production of 4(S)KHG in Various Strains

Using a transduction process employing a P1 phage [J. H. Miller, Experiments in Molecular Genetics, Cold Spring Harbor Lab. (1972)], ppc+ gene was introduced from the Escherichia coli W3110 (ATCC 14948) into the strain NHK42, to prepare strain NHK45 with no requirement of glutamic acid. pKSR101 was introduced into the strain in the same manner as in Example 2.

The strains NHK 42, 46, 48 and 45, all of which are introduced with pKSR101, were cultured in the same manner as in Example 2, and the resulting culture supernatants were assayed by HPLC to measure the yields of 4(R)HG and 4(S)HG.

HPLC Assay Conditions

Column; Lichrospher (C18) column, manufactured by Merck, Co.

Mobile phase; solution containing 10 mM sodium citrate, 10 mM anhydrous sodium sulfate (pH 2.2), 0.4% n-propanol, and 0.03% SDS.

Flow rate; 0.8 ml/min

Temperature; 40° C.

Detection; detected after the eluted solution was treated with o-phthalic aldehyde by post column labeling.

Ex=350 nm, Em=448 nm.

The results are shown in Table 3. As is apparent from the yields of 4(S)HG of each strain, a mutation for lipoate requirement, a mutation for reduced malic acid synthetase activity, and a mutation for deletion of phosphoenolpyruvate carboxylase can make a contribution to the production of 4(S)HG.

Corynebacterium glutamicum ATCC 13032 introduced with pKSR601 was cultured with agitation in an LB culture medium for 16 hours. The culture broth (0.5 ml) was added into a sterilized TC medium (5 ml) [the medium contained 100 g glucose, 0.5 g $KH_2PO_4$, 0.5 g $K_2HPO_4$, 20 g $(NH_4)_2SO_4$, 0.25 g MgSO4, 3 g urea, 100 μg biotin, 5 g corn steep liquor, 10 mg $FeSO_4.7aq$, 5 mg $MnSO_4.4$–6aq, and 20 g $CaCO_3$ per one liter of water and had been adjusted to pH 7.2], and cultured with agitation at 30° C. for 24 hours. Then, 2M glyoxylic acid solution (0.25 ml; adjusted to pH 6.4 by using NaOH) was added, and the mixture was further cultured at 37° C. for 24 hours. The culture supernatant was analyzed by HPLC in the same manner as described above to assay the yields of 4(R)HG and 4(S)HG.

The results are shown in Table 3.

TABLE 3

| Host | Plasmid | 4(R)HG(mM) | 4(S)HG(mM) |
|---|---|---|---|
| Escherichia coli NHK42 | pKSR101 | 0.1 | 14.0 |
| Escherichia coli NHK46 | pKSR101 | 0.1 | 21.9 |
| Escherichia coli NHK48 | pKSR101 | 0.0 | 1.5 |
| Escherichia coli NHK45 | pKSR101 | 0.1 | 3.7 |
| Corynebacterium glutamicum ATCC13032 | pKSR601 | 0.0 | 9.8 |

Example 6

Scale Up Production of 4(S)HG

*Escherichia coli* strain NHK 46 introduced with pKSR101 was cultured with agitation in an LB culture medium containing 1% glucose, 2% calcium carbonate. 100 μg/l lipoic acid, and 2 g/l glutamic acid at 28° C. for 13 hours. The culture broth (10 ml) was added to the same culture medium of 200 ml in a 1-liter sterilized Erlenmeyer flask and cultured with agitation at 28° C. for 13 hours. The total volume of the culture broth was added to the J2 culture medium of the composition shown in Table 4 in a 5-liter sterilized jar, and cultured at an aeration volume of 2 liter/min and agitation of 500 rpm and 33° C., while the pH of the medium was kept at pH 6.8 by using aqueous ammonia. Fourteen hours later, 2M glyoxylic acid solution (350ml; adjusted to pH 6.4 by using NaOH) was added into the jar, and further cultured at 37° C. for 60 hours while appropriately adding glucose. The culture supernatant was analyzed by HPLC in the same manner as in Example 5, and it was observed that the yield of 4(S)HG was 141.7 mM and the yield of 4(R)HG was 6 mM.

TABLE 4

Composition of J2 culture medium (per one liter; adjusted to pH 6.8)

| | |
|---|---|
| Glucose | 30 g |
| $KH_2PO_4$ | 2 g |
| $K_2HPO_4$ | 2 g |
| $(NH_4)_2SO_4$ | 10 g |
| $MgSO_4$ | 1 g |
| $FeSO_4.7aq$ | 10 mg |
| $MnSO_4.4-6aq$ | 10 mg |
| $CoCl_2$ | 1.5 mg |
| $CaCl_2$ | 15 mg |
| $NiCl_2$ | 1.5 mg |
| Ammonium molybdenate | 1.5 mg |
| Thiamin hydrochloride salt | 100 μg |
| Yeast extract | 0.5 g |
| KCl | 3 g |
| Lipoic acid | 75 μg |
| Tryptophan | 250 mg |
| Glutamic acid | 12 g |
| Isoleucine | 20 mg |
| Methionine | 10 mg |

Example 7

Purification of 4(S)HG

Employing centrifugation, microorganisms were removed from the culture broth (one liter) containing 4(S)HG and 4(R)HG as obtained in Example 6, and the resulting culture supernatant was passed through a column packed with a cation exchange resin SK1B (500 ml) ($H^+$ type, manufactured by Mitsubishi Chemical Corporation). After rinsing with water, aqueous 1N ammonia was passed through the column to fractionate an HG eluate fraction. The fractionated solution was subjected to a decoloring process on active charcoal, and half of the resulting solution was passed through a column packed with an anion exchange resin PA316 (400ml) (OH type, manufactured by Mitsubishi Chemical Corporation). After rinsing with water, 0.5N hydrochloric acid was passed through the column to fractionate an HG eluate fraction. By evaporation, hydrochloric acid was removed from the fractionated solution, and the resulting solution was concentrated to 50 ml, which was then left to stand at 4° C. for 2 days. The crystal generated in the liquid was filtered to recover 4(S)HG (7 g). By NMR analysis, mass spectrometry and optical rotation assay, the crystal was confirmed to be 4(S)HG with no 4(R)HG present. Therefore, using strain NHK46, 4(S)HG can be collected in a one-step reaction with no contamination from 4(R)HG.

Example 8

Ligation of Proline Synthase Gene to KAL Gene

Firstly, A mutant proBA gene desensitized against the proline feedback inhibition was prepared by modifying proBA (encoding proB and proA) gene coding for the proline biosynthase in the following manner.

*Escherichia coli*-derived plasmid pPRO-1 (Japanese Unexamined Patent Publication No. 3-266995) containing the proBA gene was digested with EcoRV, and the digested products were then electrophoresed on agarose gel to isolate and purify a DNA fragment containing a part of the proB gene using prep-A-Gene DNA Purification System (manufactured by Bio-Rad Co.). The fragment was ligated to a digested product obtained by digesting pUS119 (manufactured by Takara Brewery, Co.) with SmaI. The resulting ligation product was used to transform *Escherichia coil* ATCC 33625 to prepare ampicillin resistant transformants. A plasmid was extracted from one of these transformants by conventional methods for restriction analysis. It was confirmed that the plasmid was inserted with a DNA fragment of about 1 kb containing a part of the proB gene at the SmaI site of pUC119. The plasmid was defined as pBAB51.

On the basis of the nucleotide sequence of the known desensitized proB enzyme gene (proB74 mutation) [A. M. Dandekar and S. L. Uratsu, J. Bacteriol. 170, 5943 (1988)], an oligonucleotide A1 of the sequence of SEQ. ID No:3 and an oligonucleotide A2 of the sequence of SEQ. ID No:4 were synthetically prepared by conventional methods. By subsequently using a pair of the oligonucleotide A1 and M13 primer M3 (manufactured by Takara Brewery; Co.) as a primer and also using a pair of the oligonucleotide A2 and M13 primer RV (manufactured by Takara Brewery, Co.) as another primer, independently, a partial sequence of the mutant proB gene was amplified by PCR using pBAB51 as the template, in the same manner as in Example 1. The amplified DNA was electrophoresed on agarose gel and purified using a Prep-A-Gene DNA Purification System (Bio-Rad, CO.). Using a mixture of these two DNA fragments after purification as the template, PCR was again conducted using the M13 primer M3 and M13 primer RV as the primers to amplify the DNA fragment of about 1 kb containing the mutant proB gene sequence. After digestion with Eco0651 and SacII, the DNA fragment was ligated to a DNA fragment of about 6.8 kb, as recovered by digestion of pPRO-1 with Eco0651 and SacII and subsequent agarose gel electrophoresis and isolation and purification by using Prep-A-Gene DNA Purification System (Bio-Rad Co.). Using the ligation product, the *Escherichia coli* ATCC 33625 was transformed to prepare tetracycline resistant transformants. Several of these transformants and the *Escherichia coli* ATCC 33625 carrying pPRO-1 were replicated on an M9 minimal agar culture medium with addition of 3,4-dehydroproline (100 mg). All the transformants were grown, but the *Escherichia coli* ATCC 33625 carrying the pPRO-1 was not grown. It was confirmed that a plasmid in which the proB gene of the pPRO-1 was modified into a desensitized type was constructed. Using conventional methods, plasmids were extracted from these transformants for restriction analysis, which indicates that all the plasmids had the same structure. The plasmid was defined as pKSR24.

Figure 3:
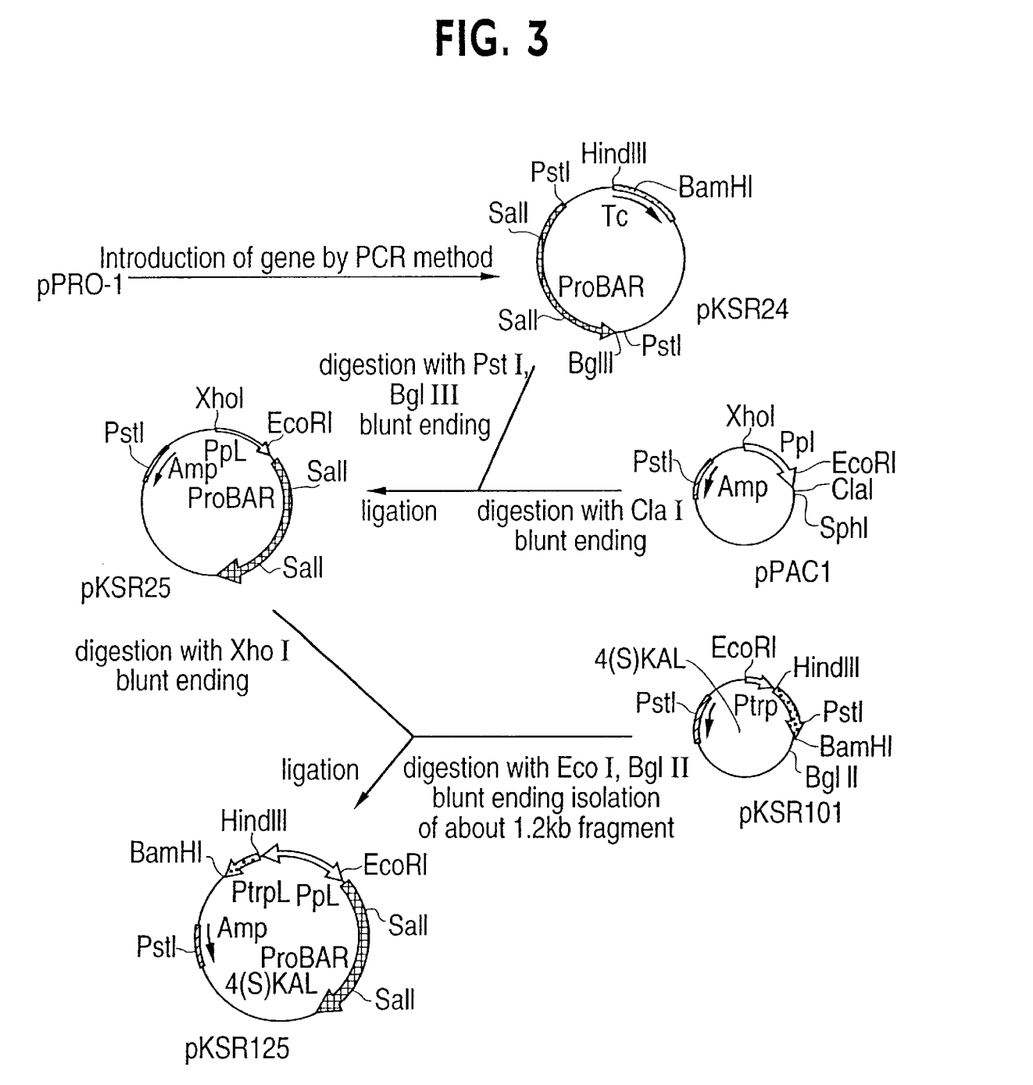
FIG. 3 depicts the construction process of plasmid pKSR125 and a restriction map of the plasmid.

The pKSR24 thus prepared was digested with PstI and BglII, and was blunt ended by using a DNA blunting kit (manufactured by Takara Brewery, Co.). By agarose gel electrophoresis and with Prep-A-Gene DNA Purification System (Bio-Rad Co.), a DNA fragment of about 2.9 kb containing the mutant proBA gene was isolated and purified. A ClaI digest of pPACl as a plasmid with a high-temperature induction type promoter and restriction sites shown in FIG. 3 was ligated to the DNA fragment after the fragment was blunt ended by means of a DNA blunting kit. Using the ligation product, the *Escherichia coli* ATCC 33625 was transformed, and plasmids were extracted from the transformants to recover pKSR25 having a structure where the mutant proBA was inserted downstream of the high-temperature induction type promoter of pPACl so that the transcription direction of the mutant might be a sequential direction.

pKSR101 prepared in Example 1 was digested with EcoRI and BdlII, and was then blunt ended by using a DNA blunting kit, and a DNA fragment containing the KAL gene of about 1.2 kb was isolated and purified by using agarose gel electrophoresis and a Prep-A-Gene DNA Purification System (manufactured by Bio-Rad Co.). The DNA fragment of about 1.2 kb ligated with a DNA fragment recovered by digesting pKSR25 with XhoI and blunt ending the digested product with a DNA blunting kit. Using the ligation product, the *Escherichia coli* ATCC 33625 was transformed, and ampicillin resistant transformants were recovered from the transformants. Several transformants were assayed for 3,4-dehydroproline resistance and KAL activity. It was confirmed that all the transformants had 3,4-dehydroproline resistance and KAL activity. By conventional methods, plasmids were extracted from eight such transformants for restriction analysis, which indicates that all the plasmids had the same structure. The plasmids was defined as pKSR125. The plasmid construction process and the restriction map of pKSR125 are shown in FIG. 3.

Example 9

4(S) HYP Production by Culturing with Addition of Glyoxylic Acid

A mutant strain resistant to azetidine-2-carboxylic acid as a proline analog was induced from the strain NHK46 prepared in Example 2 as follows. The strain NHK46 cultured in the same manner as in Example 2 was subjected to a mutagenesis in the same manner as in Example 2, and then smeared on an M9 minimal agar culture medium with addition of 0.5% glucose, 0.5 g/l glutamic acid, 100 μg/l lipoic acid, and 100 mg/l azetidine-2-carboxylic acid, and incubated at 37° C. for 2 days. Among the resulting colonies, larger ones were harvested, to obtain azetidine-2-carboxylate resistant mutant strain NHK 47.

pKSR125 prepared in Example 8 was introduced into the strains NHK46 and NHK47 to obtain transformants by using ampicillin resistance as the marker. The individual transformants and the strain NHK 46 carrying pKSR101 (prepared in Example 2) were cultured in the same manner as In Example 2, and these culture supernatants were assayed by HPLC to determine 4(S)HYP.

HPLC Assay Conditions

Column: Shiseido CapcellPak-C18 (4.6×150 mm)

Mobile phase: A; 10 mM sodium citrate (pH 4), B; a mixture solution of equal volumes of A and methanol Flow rate; 1.5 ml/min Temperature; 50° C.

| Gradient time schedule of mobile phase | |
|---|---|
| Time (min) | B (vol %) |
| 0–10 | 0–8 |
| 10–20 | 8–80 |
| 20–21 | 80–100 |
| 21–23 | 100 |
| 23–24 | 0 |

Detection: detection of fluorescence at Ex=470 mm and Em=530 nm

The results are shown in Table 5.

TABLE 5

| Host | Plasmid | 4(R)HYP(mM) | 4(S)HYP(mM) |
|---|---|---|---|
| *Escherichia coli* NHK46 | pKSR101 | 0.0 | 0.0 |
| *Escherichia coli* NHK46 | pKSR125 | 0.0 | 2.1 |
| *Escherichia coli* NHK47 | pKSR125 | 0.0 | 10.3 |

Example 10

4(S)HYP Production by Two-step Reaction

By the transduction method with P1 phage, isocitrate dehydrogenase deletion mutation (icd) was introduced into the *Escherichia coli* ATCC 33625 from an *Escherichia coli* mutant strain EB106 with deletion of isocitrate dehydrogenase deletion [supplied from the *E. coli* Genetic Stock Center, Yale University, New Haven, Conn., USA], to prepare strain NHK3. The mutant strain expressed glutamic acid requirement because of the icd mutation.

Figure 4:
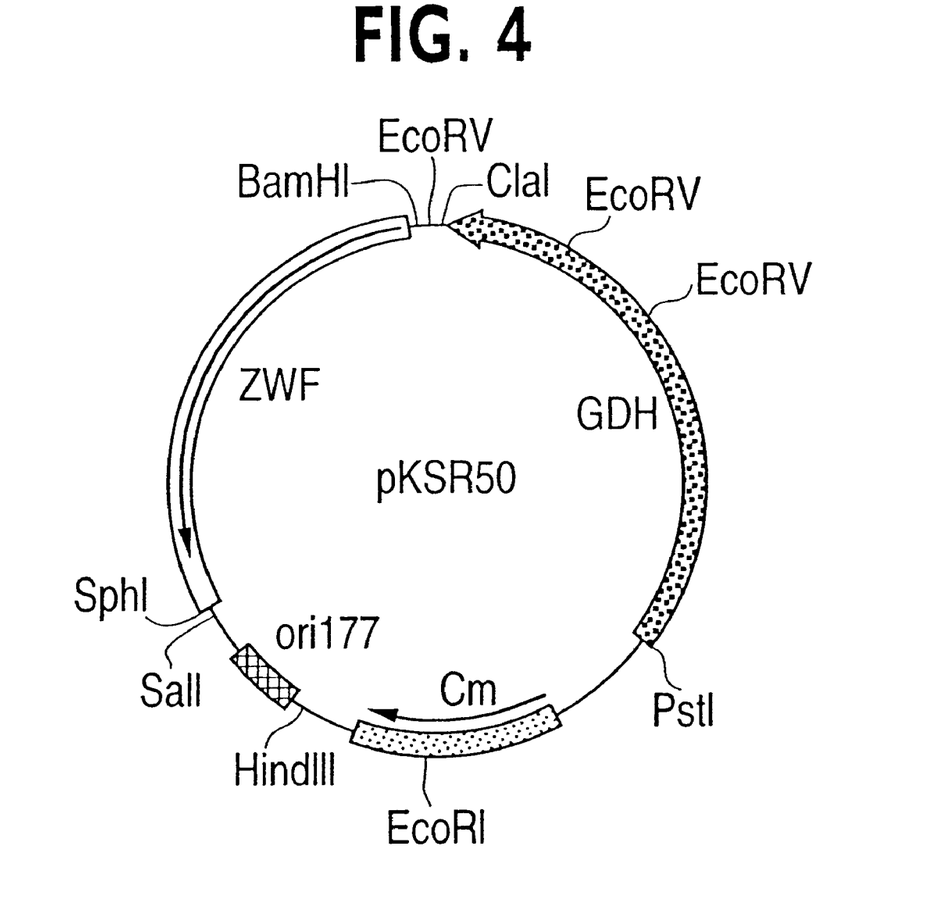
FIG. 4 depicts plasmid pKSR50 and a restriction map of the plasmid.

Using pKSR25 prepared in Example 8, the *Escherichia coli* ATCC 33625 and NHK3 were individually transformed to obtain individually transformants using as the marker ampicillin resistance. Furthermore, using plasmid pKSR50 (FIG. 4) derived from pACYC177, carrying a 4.2-kb DNA fragment carrying the glutamate dehydrogenase gene (gdh) of *Escherichia coli* interposed between the PstI and ClaI sites, and an about 3-kb DNA fragment, carrying the glucose-6-phosphate dehydrogenase gene (zwf), interposed between the BamHI and SphI sites, the *Escherichia coli* NHK3 carrying pKSR25 (NHK3/pKSR25 strain) was transformed to obtain strain NHK3 carrying pKSR50 and pKSR25 (NHK3/pKSR50+pKSR25) using as the marker the resistance against ampicillin and chloramphenicol. Into a mutant strain NHK23 of a mutation type (icd, sucA, putA, eda) of *Escherichia coli* K-12 strain were also introduced pKSR50 and pKSR25 to obtain a strain NHK23/pKSR50+ pKSR25.

In the same manner as in Example 2, *Escherichia coli* ATCC 33625, and the NHK3, ATCC33625/pKSR25, NHK3/pKSR25, NHK3/pKSR50+pKSR25 and NHK23/pKSR50+pKSR25, all having been prepared as described above, were similarly cultured in a T culture medium at 30° C. for 24 hours The resulting culture supernatant containing 4(S)KHG prepared in Example 4 after filtration and sterilization through a Millipore filter was added to the resulting culture to a final 4(S)KHG concentration of 40 mM, and the mixture was further cultured with agitation at 37° C. for 24 hours. 4(S)HYP in the culture broth was assayed by the following method. To 80 μl of the culture supernatant was added a methanol solution (100 μl) containing 1M borate buffer (pH 9.6; 20 μl) and 6 mg/ml NBD-Cl (7-chloro-4-nitrobenzo-2-oxa-1,3-diazole chloride) for reaction at 60° C. in darkness for 20 minutes, followed by addition of 1N HCl (50 μl) to the reaction solution to terminate the reaction. The mixture was filtered through a Millipore filter, and the filtrate was assayed by HPLC in the same manner as in Example 9 to assay 4(S)HYP. The results are shown in Table 6.

Alternatively, *Corynebacterium glutamicum* KY 10912 was cultured with agitation in an LB culture medium for 16 hours. The culture broth was then added into a sterilized TC culture medium of 5 ml and cultured with agitation at 30° C. for 24 hours. The culture supernatant carrying 4(S)KHG prepared in Example 4 after filtration and sterilization through a Millipore filter was added to the culture to a final 4(S)KHG concentration of 40 mM, and further cultured with agitation at 37° C. for 24 hours. The culture supernatant was analyzed by HPLC as in Example 9 to assay 4(S)HYP. The results are shown in Table 6.

TABLE 6

| Host | Plasmid | 4(S)HYP(mM) |
|---|---|---|
| E. coli ATCC33625 | none | 0.0 |
| E. coli ATCC33625 | pKSR25 | 0.4 |
| E. coli NHK3 | none | 0.0 |
| E. coli NHK3 | pKSR25 | 0.9 |
| E. coli NHK3 | pKSR50 + pKSR25 | 1.6 |
| E. coli NHK23 | pKSR50 + pKSR25 | 5.8 |
| C. glutamicum KY10912 | none | 1.0 |

In accordance with the present invention, (S)-4-hydroxy-2-ketoglutaric acid and compounds from the precursor (S)-4-hydroxy-2-ketoglutaric acid, for example (2S,4S)-4-hydroxy-L-glutamic acid and (2S,4S)-4-hydroxy-L-proline, can be produced in an industrially advantageous manner. (2S,4S)-4-hydroxy-L-proline has biological actions including anti-tumor cell activity [Cancer Res. 48, 2483(1988)] and anti-mast cell activity (Japanese Unexamined Patent Publication No. 63-218621). (S)-4-hydroxy-2-ketoglutaric acid and (2S,4S)-4-hydroxy-L-glutamic acid are useful as raw materials to synthesize the proline.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. A method for producing (2S,4S)-4-hydroxy-L-proline, comprising:
   (a) reacting a biocatalyst, having activity to convert (S)-4-hydroxy-2-ketoglutaric acid into (2S,4S)-4-hydroxy-L-proline, with (S)-4-hydroxy-2-ketoglutaric acid in an aqueous medium, and
   (b) collecting (2S,4S)-4-hydroxy-L-proline generated in the aqueous medium.

2. A method according to claim 1, wherein the biocatalyst is a culture or cells or treated products of a microorganism.

3. A method according to claim 2, wherein the microorganism belongs to genus Escherichia or Corynebacterium.

4. A method according to claim 2, wherein the microorganism is a microorganism having resistance to proline analogs.

5. A method according to claim 2, wherein the microorganism is a microorganism having glutamic acid requirement.

6. Recombinant plasmid pKSR101.

7. A biologically pure culture of *Escherichia coli* FERM BP-5919.

8. A biologically pure culture of *Escherichia coli* FERM BP-5920.

9. A biologically pure culture of *Escherichia coli* FERM BP-5921.

10. A biologically pure culture of *Escherichia coli* FERM BP-5922.

11. A biologically pure culture of *Escherichia coli* FERM BP-5923.

12. A biologically pure culture of *Escherichia coli* FERM BP-6382.

* * * * *